United States Patent
Ptchelintsev

Patent Number: 5,922,335
Date of Patent: *Jul. 13, 1999

[54] USES FOR ASCORBYL-PHOSPHORYL-CHOLESTEROL IN TOPICAL COMPOSITIONS

[75] Inventor: Dmitri Ptchelintsev, Mahwah, N.J.

[73] Assignee: Avon Products, Inc., New York, N.Y.

[*] Notice: This patent is subject to a terminal disclaimer.

[21] Appl. No.: 09/126,191

[22] Filed: Jul. 30, 1998

Related U.S. Application Data

[63] Continuation-in-part of application No. 08/853,271, May 9, 1997, which is a continuation-in-part of application No. 08/440,765, May 15, 1995, abandoned.

[51] Int. Cl.$^6$ .................................................. A61K 7/00
[52] U.S. Cl. ........................... 424/401; 424/59; 424/60; 424/405; 514/474; 514/169; 514/171; 514/553; 514/844; 514/944
[58] Field of Search .................... 424/401, 59, 60, 424/70.1, 70.2, 405; 514/474, 169, 171, 880, 844, 553, 944

[56] References Cited

U.S. PATENT DOCUMENTS

| | | |
|---|---|---|
| 3,151,127 | 9/1964 | Spanel . |
| 4,254,105 | 3/1981 | Fukuda . |
| 4,564,686 | 1/1986 | Ogata . |
| 4,919,921 | 4/1990 | Hatae . |
| 4,939,128 | 7/1990 | Kato et al. . |

(List continued on next page.)

FOREIGN PATENT DOCUMENTS

| | | |
|---|---|---|
| 0 236 120 A2 | 9/1987 | European Pat. Off. . |
| 0 503 582 A1 | 9/1992 | European Pat. Off. . |
| 92104149 | 9/1992 | European Pat. Off. . |

OTHER PUBLICATIONS

Menon, et al., Structural Basis for the Barrier Abnormality Following Inhibition of HMG CoA Reductose in Murine Epidermis, J. Invest. Dermol. vol. 98, pp. 209–219 (1992).

Hans Steinhart, et al, Pro–and Antioxidative Effect of Ascobic Acid on L–Tryptophan in the System FE3+/Ascorbic Acid/02, J. Agric. Food Chem., vol. 41, pp. 2275–2277 (1993).

Sakamoto, et al., Measurement Method of Efficacy of Anti-dandruff Cosmetics and Development of the New Active Commerical Product, IFSCC, Yokohama, vol. B206, pp. 823–864 (1993).

Juva, Anal. Biochem., vol. 15, pp. 77–83 (1966).

Sagarin, Cosmetics, Science and Technology, 2nd Ed. vol. 1, pp. 32–43 (1972).

J. Cosmet, Cham., vol. 29, p. 185 (1978).

Szoka et al., Proc. Nat. Acad. Sciences, vol. 75, pp. 4194–4198 (1978).

Evans, Chromatographia, vol. 13, pp. 5–10 (1980).

Booth, Biochem. Biophys. Acta, vol. 675, pp. 117–122 (1981).

Mezei, J. Pharmaceut. Pharmacol., vol. 34, pp. 473–474 (1982).

(List continued on next page.)

Primary Examiner—Gollamudi S. Kishore
Attorney, Agent, or Firm—Ohlandt, Greeley Ruggiero & Perle, L.L.P.

[57] ABSTRACT

Novel uses of 3'-(L-ascorbyl-2-o-phosphoryl)-cholesterol, 3'-(L-ascorbyl-3-o-phosphoryl)-cholesterol, structural or functional isomers thereof and salts thereof (referred to collectively as "APC compounds") are disclosed. Such novel uses include a method of reducing epidermal synthesis of abnormal elastin, especially epidermal synthesis of abnormal elastin that results from exposure to UV radiation. Also disclosed is a novel method of stimulating keratinocyte formation of triglycerides. In addition, a novel method of achieving antioxidant activity, both in the skin and also in topical compositions, is disclosed.

17 Claims, 1 Drawing Sheet

U.S. PATENT DOCUMENTS

| | | |
|---|---|---|
| 4,956,355 | 9/1990 | Prendergast . |
| 4,960,764 | 10/1990 | Figueroa, Jr. et al. . |
| 5,053,222 | 10/1991 | Takasu et al. . |
| 5,061,733 | 10/1991 | Bryce et al. . |
| 5,075,333 | 12/1991 | Bryce et al. . |
| 5,110,950 | 5/1992 | Seib et al. . |
| 5,122,536 | 6/1992 | Perricone . |
| 5,229,378 | 7/1993 | Ogata et al. . |
| 5,306,713 | 4/1994 | Suetsugu et al. . |
| 5,308,621 | 5/1994 | Taylor et al. . |
| 5,318,987 | 6/1994 | Weithmann et al. . |
| 5,336,485 | 8/1994 | Fariss . |
| 5,474,991 | 12/1995 | Ogata et al. . |
| 5,474,992 | 12/1995 | Ogata et al. . |
| 5,478,815 | 12/1995 | Ogata . |
| 5,480,909 | 1/1996 | Sanko . |
| 5,508,275 | 4/1996 | Weithmann et al. . |
| 5,516,793 | 5/1996 | Duffy . |
| 5,556,842 | 9/1996 | Shimizu et al. . |
| 5,574,063 | 11/1996 | Perricone . |
| 5,607,968 | 3/1997 | Ptchelintsev . |
| 5,621,008 | 4/1997 | Ptchelintsev . |
| 5,660,976 | 8/1997 | Ishimura et al. . |
| 5,683,704 | 11/1997 | Ohba et al. . |
| 5,703,122 | 12/1997 | Duffy . |

OTHER PUBLICATIONS

Mezei, Topics in Pharmaceutical Sciences, Breimer et al. Eds., pp. 345–358, Elsevier Science Publishers BV, New York (1985).

Rainsford, Antiflammatory and Anti–Rheumatic Drugs, vol. I–III, CRC Press, Boca Raton, Florida (1985).

McCutcheon, Detergents and Emulsifiers, North American Edition, pp. 317–324 (1986).

Diploses et al., J. Soc. Cosmetics Chemists, vol. 43, pp. 93–100 (1992).

USES FOR ASCORBYL-PHOSPHORYL-CHOLESTEROL IN TOPICAL COMPOSITIONS

RELATED APPLICATIONS

This application is also a continuation-in-part of U.S. patent application Ser. No. 08/853,271 filed May 9, 1997, still pending, which is a continuation-in-part of U.S. patent application Ser. No. 08/440,765, filed May 15, 1995, which has been abandoned.

FIELD OF THE INVENTION

This invention relates to the 3'-(L-ascorbyl-2-o-phosphoryl)-cholesterol, 3'-(L-ascorbyl-3-o-phosphoryl)-cholesterol, and their derivatives (hereinafter collectively referred to as either "Ascorbyl-Phosphoryl-Cholesterol" or "APC compound(s)"). Specifically, this invention relates to novel uses of APC compounds. More specifically, this invention relates to novel methods of improving the condition of the skin by decreasing production of abnormal elastin, by increasing keratinocyte triglyceride biosynthesis, stimulating collagen synthesis and by providing antioxidant activity. All of the foregoing is accomplished by topically applying APC compounds. Furthermore, this invention also relates to a novel method of providing antioxidant protection for topical compositions by incorporating APC compounds.

1. Background of the Invention

The skin contains an intricate and elaborate network of fibers, elastin, that possess a high degree of elasticity. Over time, and especially as result of exposure to ultraviolet radiation, the amount of elastin production becomes elevated. However, rather than increasing the elasticity of skin, this increased production of elastin actually results in an elevated production of abnormal elastin. These abnormal elastin fibers exhibit less elasticity, and the elastin fiber system formed therefrom fails to have the same quality of organization as found during periods of normal elastin production. Hence, as indicated above, rather than enhancing the degree of elasticity exhibited by the skin, the increased elastin production results in a greater degree of wrinkling and skin sagging.

In addition, triglycerides have a role in maintaining a desired level of good skin condition and appearance. Triglycerides serve as a source of fatty acids for the production of bilayer lipids. Bilayer lipids, in turn, are ultimately incorporated into barrier lipids. Barrier lipids are produced by keratinocytes of the skin and are responsible for providing a primary defense against external assaults of many kinds, such as microbial invasion. It is believed that by stimulating triglyceride synthesis and subsequently increasing the amount of triglycerides available for synthesizing barrier lipids, the overall condition and appearance of the skin will improve.

It is well-known and accepted that exposure to conditions that generate free radicals can lead to damage both to biological and non-biological systems. In biological systems, free radical formation may lead to destruction of tissues or faulty production of new tissue. In non-biological systems, such as topical compositions, the formation of free radicals results in degradation of components. This degradation of components may result in decreased potency of the topical composition for its intended purpose. In addition, free radical formation often results in malodor and discoloration of the composition that is aesthetically displeasing to consumers.

Collagen is an important component in skin having texture and appearance that is desired by consumers. It is believed that by stimulating collagen synthesis by human fibroblasts, overall the overall condition of the skin thus treated will improve.

2. Description of the Prior Art

U.S. Pat. Nos. 5,061,733 and 5,075,333 to Bryce et al. describes the use of tetrahydronapthalene and indane compounds to accelerate repair of dermal photodamage associated with actinic elastosis.

U.S. Pat. No 5,474,991 to Ogata et al. describes a phosphoric acid diester of ascorbic acid and a tocopherol derivative that affects lipid metabolism and plasma levels of triglycerides, non-esterified fatty acids, total cholesterol, esterified cholesterol, free cholesterol, total lipid, lipid peroxides, high-density lipoproteins and low-density lipoproteins. However, the compound disclosed in this patent is disclosed as lowering plasma levels of triglycerides.

In co-pending U.S. application Ser. Nos. 08/837,282 and 08/853,271, the entire disclosures of which are incorporated herein by reference, applicant discloses stable topical applications of 3'-(L-ascorbyl-2-o-phosphoryl)-cholesterol, 3'-(L-ascorbyl-3-o-phosphoryl)-cholesterol, and their derivatives that provide means of covalently and bioreversibly coupling cholesterol and L-ascorbic acid. In these co-pending applications, applicant also discloses that APC compounds stimulate collagen production in cultured human skin fibroblasts.

The use of L-ascorbic acid as an antioxidant in food preparations is known. For example, Steinhart, *Pro- and Antioxidative Effect of Ascorbic Acid on L-Tryptophan in the Fe3+/Ascorbic Acid/O*, J. Agric. Food Chem., Vol. 41, pages 2275–2277 (1993) describes the use of L-ascorbic acid as an antioxidant that functions in food to remove free radicals and undergoing rapid oxidation.

The benefits of cholesterol for skin barrier repair are known. For example, Menon, *Structural Basis for the Barrier Abnormality Following Inhabitations of HMG CoA Reductase in Murine Epidermis*, J. Invest. Dermatol., Vol. 98, pages 209–219 (1992), describes deficiencies in the skin barrier repair mechanism when cholesterol synthesis is inhibited by regulation of HMG CoA reductase.

Free L-ascorbic acid in topical preparations demonstrates poor stability and tends to break down due to partially oxidative and non-oxidative degradation. The degraded ascorbic acid loses activity and the resultant product loses aesthetic appeal since it exhibits a cosmetically undesired brown color. Issued patent U.S. Pat. No. 5,607,968 to applicant discloses a method of making ascorbic acid-phosphoryl derivatives, which incorporate straight chain ($C_2$ to $C_{18}$) alkyl groups.

Although the individual benefits of ascorbic acid and cholesterol are known, mechanical mixing of L-ascorbic acid and cholesterol results in an unstable product due to the instability of L-ascorbic acid.

U.S. Pat. No. 4,939,128 to Kato is directed to the use of phosphoric acid esters of ascorbic acid for the treatment of systemic diseases, not for cosmetics, topical dermatological or skin uses. This patent teaches that certain phosphoric acid esters of ascorbic acid display improved oxygen scavenging properties. However, the specific mention of a cholestenyl group suggests that conjugates of L-ascorbic acid and cholesterol were neither practical nor desired.

Attempts have been made to conjugate ascorbic acid with a glycyrrhetic group as described in European Application No. 92104149.7; and with a tocopheryl group as indicated by U.S. Pat. No. 3,151,127. For example, U.S. Pat. Nos.

4,564,686, 5,306,713, and 5,474,992 describe phosphate diesters of tocopheryl and ascorbic acid, and derivatives thereof, as having anti-oxidant activity. Also, U.S. Pat. No. 5,478,815 describes the use of ascorbyl tocopherol phosphate compounds and derivatives as liver protectants. In addition, U.S. Pat. No. 5,683,704 to Ohba et al. describes cosmetic compositions having dl-α-tocopheryl 2-L-ascorbyl phosphate.

Also, Sakamoto, *Measurement Method of Efficacy of Antidandruff Cosmetics and Development of the New Active Commercial Product,* IFSCC, Yokohama, Vol. B206, pages 823–864 (1993) describes the use of tocopheryl coupled to L-ascorbic acid. The coupled tocopheryl is an antioxidant preservative for the ascorbyl group, but the use of the ascorbyl-tocopheryl as a skin therapeutic is questionable since, unlike cholesterol, tocopheryl is not a natural substrate for the skin.

OBJECTS OF THE INVENTION

It is an object of the present invention to provide a novel method of inhibiting elevated production of abnormal elastin.

It is also an object of the present invention to provide such a novel method for inhibiting the elevated production or abnormal elastin that results from ultraviolet exposure.

It is another object of the present invention to provide a novel method for retarding the dermatological aging associated with elevated production of abnormal elastin.

It is still another object of the present invention to provide a method of enhancing the condition and appearance of the skin by stimulating triglyceride synthesis by keratinocytes.

It is yet another object of the present invention to provide a topical composition that enhances the condition and appearance of the skin by stimulating triglyceride synthesis.

It is still yet another object of the present invention to provide an elegant topical composition that may be topically applied to stimulate keratinocyte triglyceride synthesis and thereby increase the condition, feel, tone and appearance of the skin.

It is a further object of the present invention to provide a novel method of providing antioxidant protection to topical compositions.

It is still a further object of the present invention to provide compositions useful for practicing the methods described herein.

These and other objects of the present invention will become evident from the invention described below.

DETAILED DESCRIPTION OF THE PREFERRED EMBODIMENTS

Figure 1:
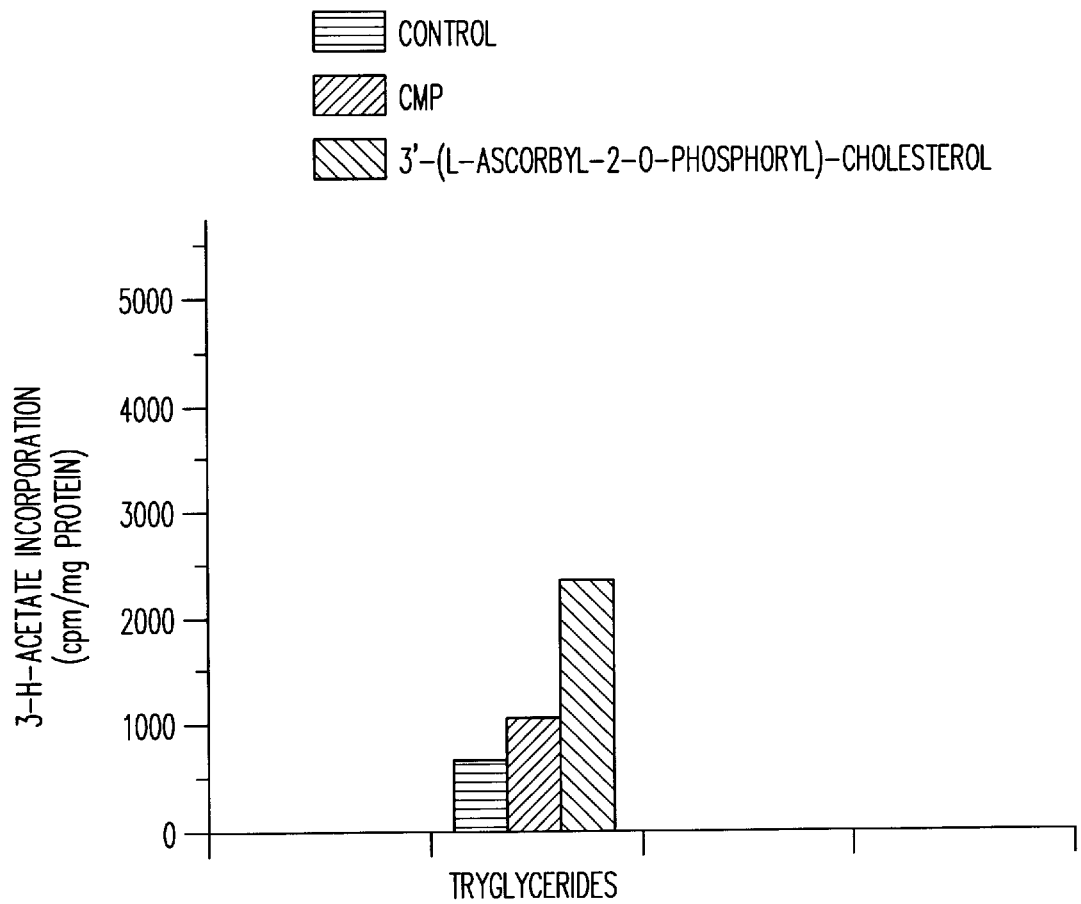
FIG. 1 illustrates that 3'-(L-ascorbyl-2-o-phosphoryl)-cholesterol significantly increases triglyceride synthesis in cultured human keratinocytes.

The present invention includes a compound that is a derivative of L-ascorbic acid. The compound is formed by a coupling of L-ascorbic acid and cholesterol. The novel compound, can be easily included in a topical vehicle, an is selected from the group consisting of 3'-(L-ascorbyl-2-o-phosphoryl)-cholesterol, 3'-(L-ascorbyl-3-o-phosphoryl)-cholesterol, functional or structural isomers thereof and salts thereof ("APC compounds"). The exemplary compounds include functional or structural isomers of 3'-(L-ascorbyl-2-o-phosphoryl)-cholesterol (Formula I) such as 3'-(L-ascorbyl-3-o-phosphoryl)-cholesterol (Formula II). Both formulas are illustrated below.

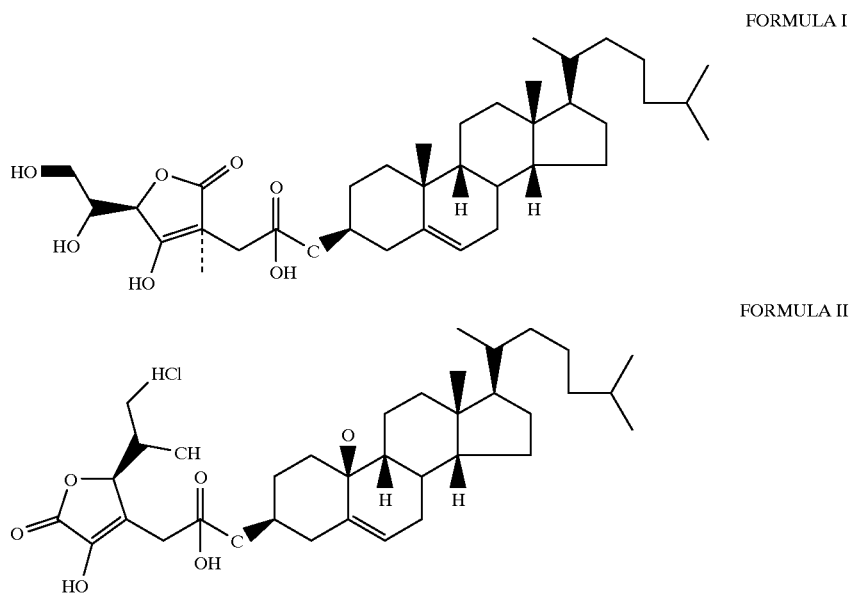

The L-ascorbic acid is covalently bound to the cholesterol by phosphoryl or phosphates so that the ascorbic acid derivatives set forth above are also called "Ascorbyl-Phosphoryl-Cholesterol" or "APC compounds".

In the APC compounds of the present invention, the conjugated ascorbic acid becomes resistant to degradation. The cholesteryl group serves as a carrier moiety and facilitates delivery of polar ascorbic acid through the non-polar outermost protective layer of skin (i.e., the stratum corneum) and increases the bioavailability of the ascorbic acid in the topical application.

Natural enzymes, such as phosphatases present in the skin, gradually cleave the phosphoryl or phosphate linkage between cholesterol and ascorbic acid, resulting in sustained release of free L-ascorbic acid and cholesterol into the stratum corneum. The released cholesterol is a natural substrate for skin and supplements that otherwise produced by the body. Topically applied cholesterol improves elasticity, tone and resistance to drying.

The basic topical formula may comprise from about 0.0001 to about 100, with all ranges set forth herein as weight percent (wt %), of the APC compound. If the APC compound is further incorporated into a vehicle that is suitable for topical use (hereinafter "topical vehicle"), then the resultant topical formulation may comprise from about 0.0001 to about 99 weight percent of the APC compound. In a preferred embodiment, about 0.05 to about 50 weight percent of the APC compound is in a topical vehicle. In a more preferred embodiment, about 0.10 to about 20 weight percent of the APC compound is combined with a topical vehicle, and in an even more preferred embodiment about 1.0 to about 10 weight percent of the L-ascorbic acid derivative is combined with a topical vehicle.

Salts of the APC compound, namely ammonium, calcium, lithium, potassium or sodium can be incorporated, either individually or with the L-ascorbic derivative, into a topical vehicle. A salt with an organic amine, such as ethanolamine, may also be used in combination with the APC compound.

"A suitable topical vehicle" means a vehicle or carrier that are suitable for use in direct contact with human tissues, especially human skin, without undue toxicity. Examples of suitable topical vehicles include conventional emulsions, lotions, creams or gels.

A first or more basic lotion comprises about 0.10 to about 20.0 weight percent of the APC compound, and the remainder is or includes water. Most preferably, the APC compound is 3'-(L-ascorbyl-2-o-phosphoryl)-cholesterol (Formula I) or 3'-(L-ascorbyl-3-o-phosphoryl)-cholesterol (Formula II) and, preferably, the APC compound is a functional or structural isomer and/or salts thereof. A second lotion has about 0.10 to about 20.0 weight percent APC compound, about 0.001 to about 1.5 weight percent thickener or thickening agent, and the remainder is or includes water. The second lotion may also include up to about 1.0 weight percent fragrance.

Examples of thickening agents suitable for use with the APC compound include xanthene gum, xanthene gum brine tolerant, hydroxypropyl cellulose, hydroxyethyl cellulose, carbopol and gum acacia, polyacrylamide isoparaffin emulsion (available from Seppic Co. under the tradename SEPPIGEL 305), vee-gum or magnesium aluminum silicate or combination thereof. The thickening agent is preferably xanthene gum or hydroxyethyl cellulose or a combination thereof.

A third lotion has, besides about 0.10 to about 20.0 weight percent APC compound, about 0.50 to about 1.40 weight percent of a thickening agent, about 0.50 to about 6.0 weight percent of an emollient, about 4.8 to about 14.5 weight percent of an emulsifier, and the remainder is or includes water. It may also include about 0.1 to about 1.0 weight percent of a preservative.

In the third lotion, the thickening agent is preferably about 0.25 to about 0.70 weight percent of xanthene gum, and about 0.25 to about 0.70 weight percent of hydroxyethyl cellulose. The emollient, which can be a humectant, preferably is glycerin. The emulsifier is preferably a combination of emulsifiers, namely about 2.0 to about 8.0 weight percent of propylene glycol decaprylate, about 1.8 to about 4.0 weight percent of Peg 40 Stearate, and about 1.0 to about 2.5 weight percent of Steareth-2. The preservative is preferably about 0.15 to about 0.20 weight percent of disodium EDTA or EDTA salt, and about 0.20 to about 0.3 weight percent of methylparaben.

A second cosmetic vehicle, a cream, comprises about 0.10 to about 20.0 weight percent of the APC compound, about 0.1 to about 1.20 weight percent of a thickening agent; about 0.1 to about 15 weight percent of an emulsifier, and the remainder is or includes water. It may also include up to about 1 weight percent of fragrance.

A second, less preferable, cream has about 0.5 to about 4.0 weight percent of an emollient, preferably glycerin; about 2.0 to about 6.0 weight percent of an emollient/humectant, preferably propylene glycol; emulsifiers, preferably about 1.8 to about 3.0 weight percent Steareth-20, about 0.8 to about 2.0 weight percent Steareth-2, about 1.0 to about 2.5 weight percent cetyl alcohol, and about 0.9 to about 3.5 weight percent glycerol mono-stearate; thickening agents, such as about 0.25 to about 0.6 weight percent xanthene gum and about 0.25 to about 0.6 weight percent hydroxyethyl cellulose; and a preservative, preferably about 0.15 to about 0.2 weight percent disodium EDTA or EDTA salt.

While such lotions or creams can be made by conventional homogenization methods, such lotions and creams can also be made by a process of microfluidization that involves co-mixing the aqueous phase and the oil phase of such creams and lotions in a high-pressure homogenizer that reduces the emulsion particle size dramatically to about 1/400th the size of those in creams and lotions prepared without applying high pressure. Microfluidization permits the preparation of elegant stable creams and lotions containing effective amounts of the APC compound without the use of traditional emulsifiers and surfactants.

With respect to the APC compound in a gel vehicle, a first or preferred gel has about 0.10 to about 20 weight percent APC compound, about 0.30 to about 2.0 weight percent thickening agent, and the remainder includes water. A second or less preferred gel has about 0.10 to about 20.0 weight percent APC compound; about 2.0 to about 6.0 weight percent of an emollient/humectant, preferably propylene glycol; about 0.4 to about 1.5 weight percent of a thickening agent, preferably hydroxyethyl cellulose; and a preservative, preferably about 0.15 to about 0.20 weight percent disodium EDTA or EDTA salt and about 0.20 to about 0.3 weight percent methylparaben.

The pH of the lotion, cream or gel formulas can be adjusted to physiologically acceptable levels with sufficient amounts (preferably about 3.0 to about 7.5 weight percent) of ammonium hydroxide, calcium hydroxide, lithium hydroxide, potassium hydroxide, sodium hydroxide, ethanolamine, diethanolamine or urea.

As stated above, an emollient used in the above lotion, cream and gel formulas is glycerin and an emollient/humectant is propylene glycol. Besides such emollients, the APC compound or the lotion, cream or gel formulas can also be combined with most other conventional emollients, such as mineral oil, petrolatum paraffin, ceresin, ozokerite, microcrystalline wax, perhydrosqualene, dimethyl polysiloxanes, methylphenyl polysiloxanes, silicone-glycol copolymers, triglyceride esters, acetylated monoglycerides, ethoxylated glycerides, alkyl esters of fatty acids, fatty acids and alcohols, lanolin and lanolin derivatives, polyhydric alcohol esters, sterols, beeswax derivatives, polyhydric alcohols and polyethers, and amides of fatty acids. Other suitable emollients can be found in Sagarin, *Cosmetics, Science and Technology,* 2nd Ed., vol. 1, pp. 32–43 (1972), the contents of which are incorporated by reference herein.

In the above formulas, the emulsifiers can be cationic, anionic, non-ionic, amphoteric, or a combination thereof. A non-ionic emulsifier is preferred. As set forth above, the non-ionic emulsifiers propylene glycol decaprylate, PEG 40 Stearate, Steareth-20, Steareth-2 and cetyl alcohol are used in various formulas. Examples of other non-ionic emulsifiers are commercially available sorbitans, alkoxylated fatty alcohols and alkyl polyglycosides. Anionic emulsifiers may include soaps, alkyl sulfates, monoalkyl and dialkyl phosphates, alkyl sulphonates and acyl isothionates. Other suitable emulsifiers can be found in McCutcheon, *Detergents and Emulsifiers,* North American Edition, pp. 317–324 (1986), the contents of which are incorporated herein by reference.

Other suitable preservatives, besides disodium EDTA, EDTA salts and methylparaben set forth above, include EDTA fatty acid conjugates, alkanols, especially ethanol, isopropyl alcohol, benzyl alcohol, parabens, sorbates, urea derivatives and isothiazolinone.

Suitable humectants include urea, PCA, amino acids, certain polyols and other compounds with hygroscopic properties.

The present invention includes topically applying an effective amount in a physiologically acceptable vehicle to a skin area, normally once or twice daily. The effective amount and the frequency of application will vary depending on the particular skin, the age and physical condition of the person, and like factors within the knowledge and expertise of those skilled in the art.

The APC compound in an amount from about 0.05 to about 25 weight percent, and more preferably from about 0.05 to about 10 weight percent, can be in topical compositions alongside keratolytic agents and skin lightening agents. The keratolytic agents may include salicylic acid and benzoyl peroxide. The skin lightening agents may include kojic acid, benzoquinone, licorice derivatives, magnesium ascorbyl phosphate, glycerhetinic acid and its derivatives.

The APC compound in an amount about 0.001 to about 25 weight percent can also be used with organic and inorganic sunscreens, such cinnamic acid derivatives (menthyl, octyl, 2-ethylhexyl, benzyl, alphaphenyl cinnamonitrile, and butyl cinnamoyl pyruvate), titanium dioxide, zinc oxide, benzylidene camphor, anthranilates, and naphtholsulphonates. The cinnamic acid derivatives are preferred.

About 0.001 to about 25 weight percent, and more preferably about 0.001 to 10 weight percent of the APC compound can be co-formulated with (a) retinoids, (b) hormonal compounds, (c) alpha-hydroxyacids or polyhydroxy alpha-hydroxy acids, or (d) alpha-keto acids.

The retinoids include, for example, retinol, retinoic acid, retinyl palmitate, retinyl propionate, retinyl acetate, isotretinoin and synthetic retinoid mimics. The hormonal compounds include, for example, estriol, estradiol, estrone or conjugated estrogens. The alpha-hydroxyacids or polyhydroxy alpha-hydroxy acids include, for example, glycolic acid, lactic acid, tartaric acid, gulonic acid and other carboxylic acids and their monomeric, polymeric, cyclic or acyclic derivatives. The alpha-keto acids include, for example, pyruvic acid, 2-oxopropanoic acid, 2-oxobutanoic acid, 2-oxopentanoic acid and the like. Oxa acids and oxa diacids, as disclosed U.S. Pat. Nos. 5,834,513 and 5,847,003, may also be used with the present invention. The disclosures of the two aforementioned U.S. Patents in their entirety are incorporated herein by reference. U.S. Pat. No. 5,834,513 discloses oxa diacids of the following formula:

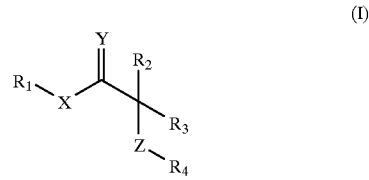

(I)

wherein, $R_4$ is $(CR_5R_6-CR_7R_8-X_1)_n-CR_9R_{10}-C(=X_2)X_3R_{11}$; n is an integer from 1 to 18, preferably from 2 to 12; $R_1$, $R_2$, $R_3$, $R_5$, $R_6$, $R_7$, $R_8$, $R_9$, $R_{10}$ and $R_{11}$, are independently hydrogen or non-hydrogen substituents, with preferred non-hydrogen substituents including alkyls, alkenyls, oxa-alkyls, aralkyls and aryls; and X, $X_1$, $X_2$, $X_3$, Y and Z are independently, O, NH or S, with preferred compounds including those in which X, $X_1$, $X_2$, $X_3$, Y and Z are each oxygen and $R_1$, $R_2$, $R_3$, $R_5$, $R_6$, $R_7$, $R_8$, $R_9$, $R_{10}$ and $R_{11}$ are each hydrogen. U.S. Pat. No. 5,847,003 discloses oxa acids of the following formula:

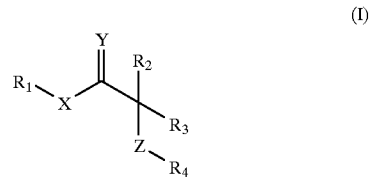

(I)

wherein, $R_4$ is $(CR_5R_6-CR_7R_8-X_1)_n-CR_9R_{10}R_{11}$; n is an integer from 1 to 18; $R_1$, $R_2$, $R_3$, $R_5$, $R_6$, $R_7$, $R_8$, $R_9$, $R_{10}$ and $R_{11}$, are independently hydrogen or non-hydrogen substituents, with preferred non-hydrogen substituents including, but not limited to, alkyls, alkenyls, oxa-alkyls, aralkyls and aryls; and X, $X_1$, Y and Z are, independently, O, NH or S, with preferred compounds including those in which X, $X_1$, Y and Z are all oxygen and $R_1$, $R_2$, $R_3$, $R_5$, $R_6$, $R_7$, $R_8$, $R_9$, $R_{10}$ and $R_{11}$ are all hydrogen. One preferred oxa diacid is 3,6,9-trioxaundecanedioic acid.

The APC compound can be used for additional benefits in topical formulations that include the following ingredients: vitamins, enzyme co-actors such as vitamin B6, vitamin B12, vitamin D3, 1,25-dihydroxy vitamin D3, vitamin B1, riboflavin, vitamin K, vitamin E, tocotrienols and their derivatives, nicotinic acid and its esters, pantothenic acid and its esters, panthenol, folic acid and its derivatives, choline, carnitine and substances without formal vitamin status or "pseudo-vitamins" such as vitamin F or cis, cis-linoleic acid, vitamin M or pteroylglutamic acid, vitamins B10 and B11, sesame seed factor, termitin, penicin, insectine, hypomycin and mycoine, vitamin L or anthranilic acid, vitamin L2 or adenylthiomethyl-pentose, myoinositol or cis-1,2,3,5-trans-4-6-cyclohexanehexol and its esters, especially phytic acid, laetrile or 1-mandelo-nitrile-beta-glucuronic acid, amygdalin, vitamin B15 or pangamic acid, vitamin B13 or orotic acid, vitamin H3 or procaine hydrochloride, vitamin U or methyl-sulfonium salts of methionine and pyrroloquinoline quinone, or effective amounts of antifungal agents such as clotrimazole, ketoconazole, miconazole, naftifine, tolnaftate, amphotericin B, nystatin, 5-fluorocytosine, griseofulvin, haloprogin, of which tolnaftate, haloprogin and miconazole are most preferred. In formulas that include one or both of the preferred, the APC compound is present in an amount from about 0.001 to about 25 and, more preferably, about 0.001 to about 10 weight percent.

About 0.001 to about 25 weight percent of the APC compound can be used with one or more of:

(1) self-tanning agents, such as dihydroxyacetone and lawsone, with the former one being most preferred;

(2) anti-mycobacterial agents, such as erythromycin, tetracyclin and related compounds, especially doxycyclin and methacyclin, cephalosporins, penicillins, macrolides, peptide compounds selected from the group consisting of novobiocin, vancomycin, oleandomycin, paromomycin, leucomycine, amphomycin with macrolide molecules preferred over the polypeptide compounds, quinolone derivatives, and other compounds which interfere with bacterial cell wall synthesis, membrane function, RNA metabolism, puline, pyrimidine and protein synthesis, respiration or phosphorylation;

(3) topical analgesics, such as lidocaine, benzocaine, butamben, butacaine, tetracaine, clove oil, eugenol, with lidocaine and benzocaine being most preferred;

(4) lipidic compounds essential for the skin's barrier function such as ceramides, essential fatty acids and their esters, especially glycerides, -hydroxy fatty acids and their esters derived with alkanols through carboxylic hydroxyl or with other fatty acids at the omega-hydroxyl, the latter type being most preferred, with phospholipids. The lipidic compounds can be added to a topical composition either as singular molecular entities or as a complex mixture of lipids derived from either synthetic, animal or plant sources;

(5) antiallergenic agents and H1 and/or H2 antihistamines, such as diphenhydramine, clemizole, antazoline, thenaldine, phenyltoloxamine citrate, tricyclic antiallergenics, such as ketotifene, dithiadene and 3-thienylsulfide of thiadene, H2-receptor blockers, especially burimamide, metiamide and cimetidien, cromolic acid and its salts;

(6) the APC compound can be used with topical anti-inflammatory agents that can reduce inflammation. These agents are at a concentration from about 0.001 to about 10 weight percent, preferably about 0.5 to about 1 weight percent. The concentration of the anti-inflammatory adjusted up or down depending upon the potency of the utilized agents. Examples of steroidal anti-inflammatories that can be used with the APC compound include hydrocortisone, hydroxytriamcilone, alpha-methyl dexamethasone, dexamethasone phosphate, beclamethasone dipropionate, hydrocortisone valerate, hydrocortisone cyclopentylpropionate, prednisolone, prednisone, and mixtures thereof, with the most preferred being prednisolone and hydrocortisone;

(7) non-steroidal anti-inflammatories can also be employed, such as described in Rainsford, *Antiinflammatory and Anti-Rheumatic Drugs,* Vols. I–III, CRC Press, Boca Raton, Fla. (1985). Specific examples of suitable non-steroidal anti-inflammatories include oxicams (e.g. piroxicam, isoxicam), fenamic acid derivatives, meclofenamic acid derivatives (e.g. sodium meclofenamate), flufenamic acid derivatives, mefenamic acid derivatives, propionic acid esters, such as ibuprofen, naproxen, benoxaprofen, flubiprofen, ketoprofen, suprofen, with ibuprofen being most preferred; pyrazolidinediones, with phenylbutazone being most preferred; the acetic acid derivatives, such as diclofenec, fenclofenac, indomethacin, sulindac, with indomethacin being most preferred; salicylic acid derivatives, such as aspirin, disalacid, benorylate, with aspirin and disalacid being most preferred.

The compositions of the present invention may also include safe anti-inflammatory products of natural origin shown to possess anti-inflammatory activity such as aloe vera extracts, extracts from genus Rubis (Rubia Cordifolio), extracts from genus Commiphom (Commiphora Mukul), Willow bark, matricarria flowers, arnica flower, comfrey root, fenugreek seed and the like known to those skilled in the art.

About 0.001 to about 25 weight percent of the APC compound can be used in formulas that contain anti-oxidants with phenolic hydroxy functions, such as gallic acid derivatives (e.g. propyl gallate), bio-flavonoids (e.g. quercetin, rutin, daidzein, genistein), ferrulic acid derivatives (e.g. ethyl ferrulate, sodium ferrulate), 6-hydroxy-2,5,7,tetra-methylchroman-2-carboxylic acid. The compositions may also contain effective concentrations of water soluble anti-oxidants such as, for example, uric acid, reductic acid, tannic acid, rosmarinic acid and catechins. Also the APC compound can be co-formulated with nitric oxide synthase inhibitors to reduce skin redness, vasodilation and inflammatory reactions, especially in response to electromagnetic and ionizing radiation or to the action of chemically or biochemically aggressive compounds. The nitric oxide synthase inhibitors can be added at concentrations from about 0.05 to about 10 weight percent, most preferably from about 1 wt % to about 3 wt %. The nitric oxide synthase inhibitors are selected from the group consisting of guanidine derivatives, especially monoaminoguianidine and methylguanidine, L-arginine derivatives, especially N-nitro-L-arginine and its esters, N-monomethyl-L-arginine, 2-iminopipperidines and other 2-iminoazaheterocycles.

Other possible anti-oxidants that topical formulation may contain are those that have one or more thiol functions (—SH) in either reduced or non-reduced form such as glutathione, lipoic acid, thioglycolic acid and other sulfhydryl compounds. The levels of sulfhydryl anti-oxidants should not exceed 0.5% for cosmetic uses of the composition, but may be higher for pharmaceutical uses as dictated by the considerations of efficacy. The composition may also include inorganic anti-oxidants, such as sulfites, bisulfites, metabisulfites or other inorganic salts and acids containing sulfur in oxidation state +4. The preferred level of inorganic sulfur-containing anti-oxidants is about 0.01 to about 0.5 weight percent, with the most preferred level about 0.1 to about 0.4 weight percent.

In addition, APC compounds may be used with other compounds known to be electron spin-traps. For example, APC compounds may be used with about 0.025 to about 5 weight percent, preferably about 0.5 to about 3 weight percent, and most preferably about 0.5 to about 1 weight percent, of such as nitrones, N-tert-butylnitrone and a -[4-pyridyl 1-oxide]-N-tertbutyl nitrone or other compounds known to form free radicals with half-life time of more than 1 minute.

About 0.001 to about 25 weight percent of the APC compound can also be used in compositions that contain insect repellents such as aliphatic, cyclic or aromatic amides, citronella oil, terpineol, cineole, neem oil and terephthalic acid and its esters. Other suitable insect repellents can be found in Technical Bulletin No. 1549 from the U.S. Department of Agriculture or in their Agricultural Handbook Nos. 69, 340 and 461.

About 0.001 to about 25 weight percent APC compound is also suitable for topical compositions that contain skin cooling compounds such as, for example, menthol, menthyl glycerol, asymmetrical carbonates, thiocarbonates and urethanes, N-substituted carboxamides, ureas or phosphine oxides such as described in *J. Cosmet, Cham.,* vol. 29, p. 185 (1978), menthyl lactate and menthone glycerine acetal.

The APC compound can be used with other cosmetic and pharmaceutical actives and exponents, such as, for example, antifungals, antiallergenic agents, depigmenting agents, antiinflammatory agents, anesthetics, surfactants, moisturizers, exfolients, stabilizers, antiseptics, lubricants, chelating agents and skin penetration enhancers. When used with these ingredients, the APC compound may provide additional dermatological and/or cosmetic benefits.

The APC compound can also be formulated in the form of micro-emulsions. The micro-emulsion system would typically contain an effective amount of the APC compound, up to 18 wt % of a hydrocarbon, up to 40 wt % of an oil, up to 25 wt % of a fatty alcohol, up to 30 wt % of a non-ionic surfactant, and up to 30 wt % of water.

The APC compound is suitable and convenient for use in topical products formulated in the form of oil-in-water or water-in-oil emulsions, ointments, sticks, sprays, tapes, patches, as multiphase emulsion compositions, such as water-in-oil-in-water type as disclosed in U.S. Pat. No. 4,254,105, incorporated herein by reference. The APC compound can also be formulated as triple emulsions of the oil-in-water-silicone fluid type as disclosed in U.S. Pat. No. 4,960,764 incorporated herein by reference.

When about 0.001 to about 25 weight percent of APC compound is used with certain chelating agents, the utility and mildness of the composition can also be enhanced. The chelating agents should be from about 0.01 to about 25 weight percent, more preferably from about 0.5 to about 10 weight percent, and most preferably from about 1 to about 5 weight percent. The examples of chelating agents include those that have a high affinity for zinc, calcium, magnesium, iron and/or copper ions, such as ethylene-diamine-tetra-acetic acid (ethylenedioxy)-diethylene-dinitrilo-tetra-acetic acid, salicylaldoxime, quinolinol, diaminocyclohexane-tetra-acetic acid, diethylene-triaminopenta-acetic acid, dimethylglyoxime, benzoin oxime, triethylenetetramine, desferrioxamine or mixtures thereof.

The APC compound has been unexpectedly and surprisingly found to be useful as active agent in topical preparations for treating signs of dermatological aging, both photoaging and intrinsic aging, including skin wrinkles such as fine wrinkling in the eye areas or "crows feet," or fine wrinkles around the mouth area, loss of skin resilience and elasticity.

The APC compound also enhances protection against UV provided by known sunscreen formulations.

The present invention also relates to a method for coupling a molecule of L-ascorbic acid to a molecule of cholesterol. The coupling preferably occurs through a bioreversible phosphate linkage at position 2 or 3 on the ascorbyl group and position 3' on the cholesteryl moiety. Resulting compositions are also contemplated by this invention.

Formula I was formed by preparing the conjugated 3'-(L-ascorbyl-2-o-phosphoryl)-cholesterol by dissolving cholesterol at −10 degrees C. in dry diethyl ether (dried with 4 A molecular sieves) containing 1.0 equivalent of triethylamine as a base. Phosphorous oxichloride (1.0 equivalent) was added to provide cholesteryl phosphorodichloridate.

The melting point of the cholesteryl phosphorodichloridate was measured as 121–122 degrees C. and infrared (KBr pellet) analysis showed P=O absorption at 1298 wavelengths and P-O-C absorption at 1019 wavelengths, with no hydroxyl absorption. Cholesteryl phosphorodichloridate was subsequently reacted for 3 hours at room temperature with 5,6-isopropylidene-L-ascorbic acid in tetrahydrofuran containing 1.0 equivalent of triethylamine. This reaction yielded a mixture of cholesteryl 5,6 isopropylidene-2-phosphorochloridate L-ascorbic acid and its isomer cholesteryl 5,6-isopropylidene-3-phosphorochloridate L-ascorbic acid.

The isomeric moisture was hydrolyzed in an aqueous solution of THF and stirred for several hours at room temperature with Amberlyst-15, a strongly acidic sulfonic acid ion exchange resin. THF and water were then removed. The final product, 3'-(L-ascorbyl-2-o-phosphoryl)-cholesterol, was extracted with ethyl acetate and neutralized with an KOH equivalent. The resulting solution was lyophilized to obtain the monopotassium salt form.

This novel method permits covalent and bioreversible coupling of cholesterol with L-ascorbic acid resulting in the stabilization of ascorbic acid, and increased bioavailability for ascorbic acid and cholesterol.

The APC compounds of the present invention are generally synthesized by (a) reacting cholesterol with a halogenophosphorelating agent, (b) coupling the resulting product with 5,6-hydroxyl protected L-ascorbic acid, (c) hydrolyzing the product with water, (d) stripping the protective group with an acidic media, and (e) precipitating the product by neutralization to salt form. The APC compound is stable in solution, exhibits anti-oxidant activity and decreases production of abnormal elastin, especially UV radiation-induced production of abnormal elastin.

Examples of the preparation and purification by reverse chromatogaphy of ascorbic cholesteryl phosphodiester acid are disclosed in applicant copending applications Ser. Nos. 08/837,282 and 08/853,271. These same applications also disclose the preparation of ascorbic cholesteryl phosphodiester chloridate and ascorbic cholesteryl phosphodiester diacid mono potassium salt. As stated above, the entire disclosures of these applications are incorporated herein by reference.

Conjugation with cholesterol converts the polar ascorbic acid to a more non-polar lipophilic ascorbyl group that is readily absorbed through the stratum corneum. Once past the stratum corneum, the absorbed compound is able to effect underlying elastin production. The benefits of bioreversed ascorbic acid and cholesterol have been previously explained. Surprisingly, the conjugated compound itself inhibits, and thereby regulates, elastin production, which enhances the integrity, elasticity and resiliency of skin.

EXAMPLE 1

This example summarizes a study which demonstrates the ability of ascorbyl-2-o-phosphoryl)-cholesterol to inhibit dermal elastin production as measured by elastin gene promotor activity. An art recognized method for evaluating the molecular events associated with increased elastin production was performed by measuring the activity of the elastin gene promoter, which is responsible for the activation of elastin gene transcription. (Bernstein, E. et al. 1995 Jour. Invest. Dermatol. 105:269–273).

Human elastin promoter molecules were linked to reporter molecules. The promoter-reporter linked molecules were then transfected into cultured dermal fibroblasts. Previous studies indicate that exposure of cultured fibroblasts to UVB radiation results in upregulation of elastin promoter activity. However, it is believed that UVA radiation may have an indirect effect on solar-induced elastosis. Hence, the degree of elastin promoter activity may be considered as an indicator of elastin production.

Solutions of 1 $\mu$M to 100 $\mu$M of each 3'-(L-ascorbyl-2-o-phosphoryl)-cholesterol and ascorbic acid were produced. These solutions were then supplied to cultured fibroblasts. The control consisted of cultured fibroblasts in media containing neither 3'-(L-ascorbyl-2-o-phosphoryl)-cholesterol nor ascorbic acid.

The cultured fibroblasts were irradiated with single, dose of UVB radiation (5.5 mJ/cm$^2$) using an FS-40 light source. The spectrum of effectiveness of the FS-40 light source is estimated at 80 to 90% attributable to UVB. It is believed that 10 to 20% of the effectiveness of the FS-40 light source is attributable to UVC. The activity attributable to UVA is believed to be negligible.

It was discovered that 3'-(L-ascorbyl-2-o-phosphoryl)-cholesterol decreased elastin promoter activity in cultured fibroblasts in a dose dependent manner. The effect of ascorbic acid on elastin promoter activity when compared to the results yielded by 3'-(L-ascorbyl-2-o-phosphoryl)-cholesterol demonstrate that 3'-(L-ascorbyl-2-o-phosphoryl)-cholesterol exhibits a far superior degree of elastin promoter inhibition and, thus, elastin formation.

In addition, the test results demonstrate that 3'-(L-ascorbyl-2-o-phosphoryl)-cholesterol inhibits elastin promoter activity for a significantly longer period of time than ascorbic acid. Table 1 below illustrates the relative activity of ascorbic acid and 3'-(L-ascorbyl-2-o-phosphoryl)-cholesterol.

TABLE A

Comparison table of percent inhibition of elastin promoter activity of 3'-(L-ascorbyl-2-o-phosphoryl)-cholesterol and ascorbic acid at 6 hour and 12 hour intervals.

| 100 µ Solution of | % Inhibition at 6 hours | % Inhibition at 12 hours |
|---|---|---|
| 3'-(L-ascorbyl-2-o-phosphoryl)-cholesterol | 43 | 34 |
| Ascorbic Acid | 23 | 0 |

EXAMPLE 2

Normal human keratinocytes (hereinafter "NHK") were cultured and then divided into three groups. Each of the three groups were grown in various media for 18.5 hours, the various media being as follows:

Group I: KGM
 0.07 mM calcium
 0.05 wt % ethanol
 0.25 wt % methanol
 1 µg/ml Vitamin E
 1 mM "cold" sodium acetate Group II: KGM
 0.07 mM calcium
 0.05 wt % ethanol
 0.25 wt % methanol
 1 µg/ml Vitamin E
 1 mM "cold" sodium acetate
 10 mM Cholesterylmonophosphate (CMP)

Group III: KGM
 0.07 mM calcium
 0.05 wt % ethanol
 0.25 wt % methanol
 1 µg/ml Vitamin E
 1 mM "cold" sodium acetate
 10 mM 3'-(L-ascorbyl-2-o-phosphoryl)-cholesterol At the conclusion of 18.5 hours, 3H-acetate sodium salt (product number NEN#003H, 6.08 ci/mMole) was added to each group at 3 uCi/ml. The three groups were incubated at 37° C. for an additional 3 hours.

At the conclusion of the incubation period, each group was washed three times with iced PBS. The cells were then collected, sonicated and aliquated for lipid extraction using Bligh/Dyer method and for protein quantification.

The lipid extracts were subfractionated by Thin Layer Chromatography. Proteins were quantitated by Bradford assay.

Triglyceride biosynthesis in cultured human keratinocytes is measured as a function of incorporation of 3-H acetate. The incorporation of 3-H acetate is expressed as counts per minute per milligram of 3-H acetate (cpm/mg 3H acetate). The results are illustrated in FIG. 1. As demonstrated 3'-(L-ascorbyl-2-o-phosphoryl)-cholesterol significantly increases triglyceride synthesis in cultured human keratinocytes.

EXAMPLE 3

Hydroxy radical scavenging activity was measured according to an art accepted method. (See Liu et al. *Antioxidant Action of Guilingji in the Brain of Rats with FeCl3-induced Epilepsy,* Free Radical Biol. & Med., (9:451–545, 1990.) Sample solutions of 3'-(L-ascorbyl-2-o-phosphoryl)-cholesterol of varying concentrations were prepared by dissolving 3'-(L-ascorbyl-2-o-phosphoryl)-cholesterol in 0.1M potassium phosphate buffer (pH=7.4). The following solutions were also prepared: 0.18M 5,5-dimethyl-1-pyrooline-N-oxide (hereinafter "DMPO") in 0.1M potassium phosphate buffer; 2 mM hydrogen peroxide (hereinafter "$H_2O_2$") in 0.1M potassium phosphate buffer; and 0.2 mM iron(II) sulfate (hereinafter "$FeSO_4$") in distilled water. Fifty (50) ml of each of the aforedescribed solutions and 50 ml of a sample solution were mixed for thirty (30) seconds and then placed in a flat cell. The Electron Spin Resonance was then measured using Free Radical Monitor JES-FR30, manufactured by JEOL, Tokyo, Japan, (hereinafter "FRM"). The FRM normalized all spectra for calculation by using an internal standard of manganese dioxide (hereinafter "$MnO_2$"). All peak heights were compared to the constant $MnO_2$ signal generated. Each sample peak height was then divided by the $MnO_2$ peak height to provide a relative peak height (hereinafter "RPH"). The results are set forth in Table C.

TABLE B

Hydroxyl radical scavenging activity of 3'-(L-ascorbyl-2-o-phosphoryl)-cholesterol as measured by Relative Peak Height (RPH) of sample as compared with $MnO_2$.

| Concentration of 3'-(L-ascorbyl-2-o-phosphoryl)-cholesterol (mg/ml) | Peak Height | Relative Peak Height (RPH) |
|---|---|---|
| 2.5000 | 0.09 | 5.6 |
| 1.2500 | 0.15 | 9.4 |
| 0.6250 | 0.49 | 30.6 |
| 0.3125 | 0.92 | 57.5 |
| 0.1563 | 1.25 | 78.1 |
| 0.0782 | 1.36 | 85.0 |
| 0.0391 | 1.60 | 100.0 |
| 0.0000 (Control) | 1.60 | 100.0 |

As demonstrated by the results set forth in Table C, 3'-(L-ascorbyl-2-o-phosphoryl)-cholesterol is an effective scavenger of hydroxyl radicals.

EXAMPLE 4

Superoxide anion scavenging ability was estimated according to the method described in the Liu et al. article noted above. Superoxide anion was generated by a hypoxanthine (hereinafter "HPX")-xanthine oxidase (hereinafter "XOD") system. The following solutions were prepared: 50 μl of 4 mM HPX in 0.1M potassium phosphate buffer; 30 μl of dimethyl sulfoxide, 50 μL of sample; 20 μL OF 4.5 mL DMPO in 0.1M potassium phosphate buffer; and, 50 μl of XOD (0.4 units/ml) in 0.1M potassium phosphate buffer. The pH of the 0.1M potassium phosphate buffer was 7.4. The solutions of HPX, DMSO, DMPO, XOD and sample were mixed and transferred into a 200 μl-capacity flat cell. Electron Spin Resonance spectra was analyzed. It was demonstrated that at the concentration of about 2.5 mg/ml, 3'-(L-ascorbyl-2-o-phosphoryl)-cholesterol inhibited the formation of the superoxide by 50%.

EXAMPLE 5

This example summarizes a study in which the ability of 3'-(L-ascorbyl-2-o-phosphoryl)-cholesterol to stimulate collagen production in cultured human skin fibroblasts is demonstrated. An art-recognized [$^3$H]-Proline Incorporation Assay was performed with differne does of 3'-(L-ascorbyl-2-o-phosphoryl)-cholesterol. Juva, *Anal. Biocheml, Vol,* 15, PAGES 77–83 (1966); Booth, *Biochem. Biophys. Acta,* Vol. 675, pages 117–122 (1981).

Fibroblasts were incubated with 0 μg/ml, 11.3 μg/ml, 22.5 μg/ml and 45 μg/ml of 3'-(L-ascorbyl-2-o-phosphoryl)-cholesterol for a total of 48 hours. After the first 24 hours [$^3$H]-labeled proline was added to the culture. Following the second 24 hour period, the cells are harvested and prepared for the collagen biosynthesis assay.

Protease inhibitors are added to prevent degradation of collagen and other proteins. The cell layer is scraped into a solution containing 0.4 M NaCl and 0.01 M Tris (pH 7.5). Extracts are sonicated to disrup cell membranes. Saparate volumes of the cell-containing solution (1 ml each) are dialyzed overnight against several changes of deionized water. The retentate is removed from dialysis and hydrolyzed in 6 N hydrochloric acid at 120 degrees C. overnight. The assay is performed using an oxidation process with 2 M chloramine-T. Samples are analyzed for radioactive counts, with represent the amount of newly synthesized [$^3$H]-labeled proline - - - an index for new collagen synthesis.

It was discovered that 3'-(L-ascorbyl-2-o-phosphoryl)-cholesterol increased production of new human skin fibroblasts in a dose dependent manner as illustrated Table D.

TABLE C

Effect of 3'- (L-ascorbyl-2-o-phosphoryl)-cholesterol on collagen biosynthesis by human skin fibroblasts.

| 3-(L-ascorbyl-2-o-phosphoryl)-cholesterol (μl/ml) | Dpm x 10$^{-3}$/ mg protein | Dpm x 10$^{-5}$/ mg DNA | Stimulation - fold Increase |
| --- | --- | --- | --- |
| 0.0 | 1.55 | 14.43 | 0 |
| 11.3 | 5.17 | 42.07 | 2.9 |
| 22.5 | 5.02 | 48.31 | 3.3 |
| 45.0 | 11.07 | 92.25 | 6.4 |

Various modifications and alterations to the present invention may be appreciated based on a review of this disclosure. These changes and additions are intended to be within the scope and spirit of this invention as defined by the following claims.

What is claimed is:

1. A method of reducing epidermal synthesis of abnormal elastin, the method comprising the step of topically applying to skin a composition comprising:

from about 0.001 to about 99 weight percent of a compound selected from the group consisting of 3-(L-ascorbyl-2-o-phosphoryl)-cholesterol, 3'-(L-ascorbyl-3-o-phosphoryl)-cholesterol, a salt thereof, a functional or structural isomer thereof, and a mixture thereof; and a vehicle.

2. The method of claim 1, wherein said salts is selected from the group consisting of ammonium, calcium, lithium, potassium, sodium and an organic amine.

3. The method of claim 1, wherein said vehicle is selected from the group consisting of a lotion, a solution, a cream and a gel.

4. The method of claim 1, wherein said composition contains from about 0.05 weight percent to about 50 weight percent of said compound.

5. The method of claim 1, wherein said composition contains from about 0.10 weight percent to about 20 weight percent of said compound.

6. The method of claim 1, wherein said composition contains from about 1.0 weight percent to about 10 weight percent of said compound.

7. The method of claim 1, wherein the pH of said composition is adjusted to a physiologically acceptable level with a sufficient amount of a second compound selected from the group consisting of ammonium hydroxide, calcium hydroxide, lithium hydroxide, potassium hydroxide, sodium hydroxide, ethanolamine, diethanolamine and urea.

8. The method of claim 1, wherein said composition further comprises at least one additional component selected from the group consisting of keratolytics, depigmenting agents, sunscreens, retinoids, hormonal compounds, alpha-hydoxy acids, polyhydroxy alpha-hydroxy acids, alpha-keto acids, vitamins, anti-mycobacterial agents, analgesics, lipidic compounds, antiallergenic agents/H1 or H2 antihistimines, anti-inflammatories, antioxidants, insect repellents, skin cooling compounds, exfolients, lubricants and antifungals.

9. A method of stimulating triglyceride synthesis in human keratinocytes, the method comprising the step of topically applying a composition comprising:

from about 0.001 to about 99 weight percent of a compound selected from the group consisting of 3'-(L-ascorbyl-2-o-phosphoryl)-cholesterol, 3'-(L-ascorbyl-3-o-phosphoryl)-cholesterol, a functional or structural isomer thereof, a salt thereof, and a mixture thereof; and a vehicle.

10. The method of claim 9, wherein said salt is selected from the group consisting of ammonium, calcium, lithium, potassium, sodium and an organic amine.

11. The method of claim 9, wherein said topical composition comprises about 0.05 weight percent to about 50 weight percent of said compound.

12. The method of claim 9, wherein said composition comprises from about 0.1 weight percent to about 20 weight percent of said compound.

13. The method of claim 9, wherein said topical composition comprises from about 1 to about 10 weight percent of said compound.

14. The method of claim 9, wherein said vehicle is selected from the group consisting of a lotion, a solution, a cream, and a gel.

15. The method of claim 9, wherein said topical composition further comprises an ingredient selected from the group consisting of keratolytics, depigmenting agents, sunscreens, retinoids, hormonal compounds, alpha-hydroxy acids, polyhydroxy alpha-hydroxy acids, alpha-keto acids, vitamins, anti-mycobacterial agents, analgesics, lipidic compounds, antiallergenic agents/H1or H2 antihistamines, anti-inflammatories, antioxidants, insect repellents, skin cooling compounds, exfolients, lubricants and antifungals.

16. A topical composition comprising:

from about 0.001 to about 99 weight percent of a first compound selected from the group consisting of 3'-(L-ascorbyl-2-o-phosphoryl)-cholesterol, 3'-(L-ascorbyl-3-o-phosphoryl)-cholesterol, a functional or structural isomer thereof, a salt thereof and a mixture thereof;

a second compound selected from the group consisting of an oxa diacid, an oxa acid, and a mixture thereof; and a vehicle.

17. The topical composition of claim 16, wherein said second compound comprises 3,6,9-trioxaundecanedioic acid.

* * * * *